US00RE48286E

(19) United States
(12) Reissued Patent
Pellicciari

(10) Patent Number: US RE48,286 E
(45) Date of Reissued Patent: Oct. 27, 2020

(54) STEROIDS AS AGONISTS FOR FXR

(71) Applicant: Intercept Pharmaceuticals, Inc., New York, NY (US)

(72) Inventor: Roberto Pellicciari, Perugia (IT)

(73) Assignee: Intercept Pharmaceuticals, Inc., New York, NY (US)

(21) Appl. No.: 16/448,503

(22) Filed: Jun. 21, 2019

Related U.S. Patent Documents

Reissue of:
(64) Patent No.: 7,138,390
Issued: Nov. 21, 2006
Appl. No.: 10/471,549
PCT Filed: Feb. 21, 2002
PCT No.: PCT/EP02/01832
§ 371 (c)(1),
(2) Date: Sep. 11, 2003
PCT Pub. No.: WO02/072598
PCT Pub. Date: Sep. 19, 2002

U.S. Applications:
(60) Provisional application No. 60/274,959, filed on Mar. 12, 2001.

(51) Int. Cl.

| | |
|---|---|
| ***C07J 9/00*** | (2006.01) |
| ***C07C 215/08*** | (2006.01) |
| ***C07C 215/10*** | (2006.01) |
| ***C07C 215/12*** | (2006.01) |
| ***C07J 41/00*** | (2006.01) |
| ***C07J 43/00*** | (2006.01) |

(52) U.S. Cl.
CPC ..... *C07J 9/005* (2013.01); *C07C 215/08* (2013.01); *C07C 215/10* (2013.01); *C07C 215/12* (2013.01); *C07J 9/00* (2013.01); *C07J 41/0055* (2013.01); *C07J 43/00* (2013.01); *Y10S 514/893* (2013.01)

(58) Field of Classification Search
CPC . C07J 9/005; C07J 41/0055; C07J 9/00; C07J 43/00; C07C 215/08; C07C 215/10; C07C 215/12; Y10S 514/893; A61P 9/10; A61P 9/00; A61P 7/00; A61P 43/00; A61P 3/06; A61P 1/16
See application file for complete search history.

(56) References Cited

U.S. PATENT DOCUMENTS

| | | | | |
|---|---|---|---|---|
| 2,615,902 | A | 10/1952 | Hirschmann et al. | |
| 3,859,437 | A | 1/1975 | Weigand | |
| 4,072,695 | A | 2/1978 | Saltzman | |
| 4,282,161 | A | 8/1981 | Guillemette et al. | |
| 4,316,848 | A | 2/1982 | Bonaldi et al. | |
| 4,379,093 | A | 4/1983 | Bonaldi et al. | |
| 4,425,274 | A | 1/1984 | Guillemette et al. | |
| 4,721,709 | A | 1/1988 | Seth et al. | |
| 4,892,868 | A | 1/1990 | Castagnola et al. | |
| 4,895,726 | A | 1/1990 | Curtet et al. | |
| 4,921,848 | A | 5/1990 | Frigerio et al. | |
| 5,061,701 | A | 10/1991 | Pellicciari et al. | |
| 5,128,481 | A * | 7/1992 | Oda et al. | 546/269.7 |
| 5,175,320 | A | 12/1992 | Pellicciari et al. | |
| 6,060,465 | A | 5/2000 | Miljkovic, Jr. et al. | |
| 6,200,998 | B1 | 3/2001 | Sahoo et al. | |
| 6,465,258 | B1 | 10/2002 | Shan et al. | |
| 6,559,188 | B1 | 5/2003 | Gatlin et al. | |
| 6,639,078 | B1 | 10/2003 | Haffner et al. | |
| 6,777,446 | B2 | 8/2004 | Houze et al. | |
| 6,906,057 | B1 | 6/2005 | Forman et al. | |
| 6,984,650 | B2 | 1/2006 | Haffner et al. | |
| 6,987,121 | B2 | 1/2006 | Kliewer et al. | |
| 6,993,380 | B1 | 1/2006 | Modarres | |
| 7,138,390 | B2 | 11/2006 | Pellicciari | |
| 7,157,101 | B2 | 1/2007 | Thosar et al. | |
| 7,786,102 | B2 | 8/2010 | Pellicciari | |

(Continued)

FOREIGN PATENT DOCUMENTS

| | | |
|---|---|---|
| EP | 0101554 A1 | 2/1984 |
| EP | 0124068 A1 | 11/1984 |

(Continued)

OTHER PUBLICATIONS

Roda et al. "Metabolism, Pharmacokinetics, and Activity of a New 6-Fluoro Analogue of Ursodeoxycholic Acid in Rats and Hamsters", Gastroenterology (1995) 108, 1204-1214 (Year: 1995).*
U.S. Appl. No. 16/832,256, filed Mar. 27, 2020, Pellicciari.
Aldini et al. "Relationship between structure and intestinal absorption of bile acids with a steroid or side-chain modification," Steroids (1996) 61(10):590-597.
Bishop-Bailey et al. "Expression and activation of the farnesoid X receptor in the vasculature," Proc. Natl. Acad. Sci. U.S.A. (2004) 101(10):3668-3673.
Center et al., "Chronic liver disease: current concepts of disease mechanisms," J. Small Anim. Pract. (1999) 40(3): 106-114.
Clerici et al., "Effect of Intraduodenal Administration of 23-Methyl-UDCA Diastereoisomers on Bile Flow in Hamsters," DiQ. Dis. Sci. (1992) 37(5):791-7.

(Continued)

*Primary Examiner* — Jerry D Johnson
(74) *Attorney, Agent, or Firm* — Cooley LLP; Ivor R. Elrifi; Chen Chen

(57) ABSTRACT

The invention relates to compounds of formula (I):

(I)

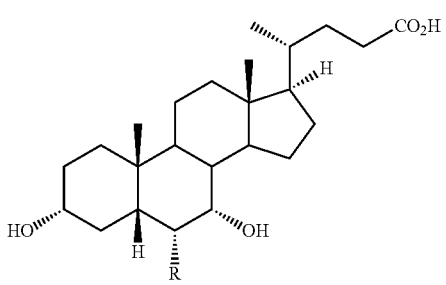

wherein R is ethyl and pharmaceutically acceptable salts, solvates or amino acid conjugates thereof. The compounds of formula (I) are useful as FXR agonists.

14 Claims, No Drawings

(56) References Cited

U.S. PATENT DOCUMENTS

| | | | |
|---|---|---|---|
| 7,858,608 | B2 | 12/2010 | Pellicciari et al. |
| 7,994,352 | B2 | 8/2011 | Ferrari et al. |
| 8,058,267 | B2 | 11/2011 | Pellicciari |
| 8,338,628 | B2 | 12/2012 | Yu et al. |
| 8,377,916 | B2 | 2/2013 | Pellicciari |
| 8,969,330 | B2 | 3/2015 | Pellicciari |
| 9,732,117 | B2 | 8/2017 | Pellicciari |
| 10,421,772 | B2 | 9/2019 | Pellicciari |
| 2002/0094977 | A1 | 7/2002 | Houze et al. |
| 2002/0120137 | A1 | 8/2002 | Forman et al. |
| 2002/0132223 | A1 | 9/2002 | Forman et al. |
| 2003/0077329 | A1 | 4/2003 | Kipp et al. |
| 2003/0130296 | A1 | 7/2003 | Pellicciari |
| 2006/0069070 | A1 | 3/2006 | Fiorucci et al. |
| 2007/0087961 | A1 | 4/2007 | Eichner et al. |
| 2008/0182832 | A1 | 7/2008 | Pellicciari et al. |
| 2009/0062526 | A1 | 3/2009 | Yu et al. |
| 2012/0160944 | A1 | 6/2012 | Dodd et al. |
| 2013/0345188 | A1 | 12/2013 | Steiner et al. |
| 2014/0024631 | A1 | 1/2014 | Pellicciari |
| 2014/0371190 | A1 | 12/2014 | Pellicciari |
| 2015/0166598 | A1 | 6/2015 | Pellicciari |

FOREIGN PATENT DOCUMENTS

| | | | |
|---|---|---|---|
| EP | 0135782 | A2 | 4/1985 |
| EP | 0186023 | A2 | 7/1986 |
| EP | 0 312 867 | | 4/1989 |
| EP | 312867 | * | 4/1989 |
| EP | 0312867 | A1 | 4/1989 |
| EP | 0 393 493 | | 10/1990 |
| EP | 0393493 | A2 | 10/1990 |
| EP | 1137940 | A1 | 10/2001 |
| EP | 1140079 | A1 | 10/2001 |
| EP | 1165135 | A1 | 1/2002 |
| EP | 1185277 | A1 | 3/2002 |
| EP | 1378749 | A1 | 1/2004 |
| EP | 1165135 | | 9/2004 |
| EP | 1473042 | | 11/2004 |
| EP | 1473042 | A1 | 11/2004 |
| EP | 1536812 | A2 | 6/2005 |
| EP | 1568706 | A1 | 8/2005 |
| EP | 1185277 | | 10/2005 |
| EP | 1947108 | A1 | 7/2008 |
| JP | H 04250093 | A | 9/1992 |
| WO | WO 97/28149 | A1 | 8/1997 |
| WO | WO 97/31907 | A1 | 9/1997 |
| WO | WO 97/36579 | A1 | 10/1997 |
| WO | WO 98/02159 | A1 | 1/1998 |
| WO | WO 99/38845 | A1 | 8/1999 |
| WO | WO 00/25134 | A1 | 5/2000 |
| WO | WO 00/28332 | A1 | 5/2000 |
| WO | WO-2000/025134 | | 5/2000 |
| WO | WO 00/37077 | A1 | 6/2000 |
| WO | WO-2000/037077 | | 6/2000 |
| WO | WO 00/40965 | A1 | 7/2000 |
| WO | WO 00/57915 | A1 | 10/2000 |
| WO | WO-2000/057915 | | 10/2000 |
| WO | WO 00/76523 | A1 | 12/2000 |
| WO | WO-2000/076523 | | 12/2000 |
| WO | WO 01/30343 | A1 | 5/2001 |
| WO | WO 02/20463 | A2 | 3/2002 |
| WO | WO-2002/020463 | | 3/2002 |
| WO | WO 02/64125 | A2 | 8/2002 |
| WO | WO-2002/064125 | | 8/2002 |
| WO | WO 02/72598 | A1 | 9/2002 |
| WO | WO 03/15771 | A1 | 2/2003 |
| WO | WO 03/15777 | A1 | 2/2003 |
| WO | WO 03/16280 | A1 | 2/2003 |
| WO | WO 03/16288 | A1 | 2/2003 |
| WO | WO 03/30612 | A2 | 4/2003 |
| WO | WO-2003/030612 | | 4/2003 |
| WO | WO 03/43581 | A2 | 5/2003 |
| WO | WO 03/80803 | A2 | 10/2003 |
| WO | WO 03/86303 | A2 | 10/2003 |
| WO | WO-2003/080803 | | 10/2003 |
| WO | WO-2003/086303 | | 10/2003 |
| WO | WO 03/90745 | A1 | 11/2003 |
| WO | WO-2003/090745 | | 11/2003 |
| WO | WO 2004/007521 | A2 | 1/2004 |
| WO | WO 2004/048349 | A1 | 6/2004 |
| WO | WO 2005/032549 | A1 | 4/2005 |
| WO | WO 2005/082925 | A2 | 9/2005 |
| WO | WO 2005/089316 | A2 | 9/2005 |
| WO | WO 2006/044391 | A1 | 4/2006 |
| WO | WO 2006/122977 | A2 | 11/2006 |
| WO | WO 2008/002573 | A2 | 1/2008 |
| WO | WO 2008/062475 | A2 | 5/2008 |
| WO | WO 2008/091540 | A2 | 7/2008 |
| WO | WO 2010/059853 | A1 | 5/2010 |
| WO | WO 2012/072689 | A1 | 6/2012 |
| WO | WO 2013/037482 | A1 | 3/2013 |
| WO | WO 2013/057741 | A2 | 4/2013 |

OTHER PUBLICATIONS

Downes et al., "A Chemical, Genetic, and Structural Analysis of the Nuclear Bile Acid Receptor FXR," Mol. Cell (2003) 11(4):1079-1092.

Fiorucci et al., "The Nuclear Receptor SHP Mediates Inhibition of Hepaptic Stellate Cells by FXR and Protects Against Liver Fibrosis," Gastroenterology (2004) 127:1497-1512.

Forman et al., "Identification of a Nuclear Receptor That Is Activated by Farnesol Metabolites," Cell (1995) 81:687-693.

Fukuch I et al., "5β-Cholane activators of the farnesol X receptor," J. Steroid Biochem. Mol. Biol, (2005) 94(4):311-318.

Haslewood et al., "Specificity and some characteristics of a 7a-hydroxysteroid dehydrogenase from E.coli," Database Accession No. 419015 (1978).

Honorio et al., "Hologram QSAR Studies on Farnesoid X Receptor Activators," Lett. Drug Des. Dis. (2006) 3(4):261-267.

Kihira et al., "Synthesis of sulfonate analogs of bile acids," Steroids (1992) 57(4):193-198.

Kim et al., "Hypocholesterolemic Effect of Bile Acid Sulfonate Analogs in Hamsters," Biol. Pharm. Bulletin (2001) 24(3):218-220.

Kliewer et al., "Peroxisome Proliferator-Activated Receptors: From Genes to Physiology," Endo J (2001) 56:239-263.

Liu et al., "Hepatoprotection by the farnesoid X receptor agonist GW4064 in rat models of intra- and extrahepatic cholestasis," J. Clin. Invest. (2003) 112(11 ): 1678-1687.

Mangelsdorf et al., "The RXR Heterodimers and Orphan Receptors," Cell (1995) 83:841-850.

Ml et al., "Structural Basis for Bile Acid Binding and Activation of the Nuclear Receptor FXR," Molecular Cell. (2003) 11:1093-1100.

Mikami et al., "Effect of some sulfonate analogues of ursodeoxycholic acid on biliary lipid secretion in the rat," J. Lipid Res, (1996) 37(6):1181-1188.

Miki et al., "Sulfonate analogues of chenodeoxycholic acid: metabolism of sodium 3α,7α-dihydroxy-25-homo-5β-cholane-25-sulfonate and sodium 3α,7α-dihydroxy-24-nor-5β-cholane-23-sulfonate in the hamster," J. Lipid Res. ( 1992) 33( 11): 1629-1637.

Nesto et al., "Thiazolidinedione Use, Fluid Retention, and Congestive Heart Failure," Diabetes Care (2004) 27( 1 ):256-263.

Pellicciari et al., "Bile Acid Derivatives as Ligands of the Farnesoid X Receptor. Synthesis, Evaluation, and Structure-Activity Relationship of a Series of Body and Side Chain Modified Analogues of Chenodeoxycholic Acid," J. Med. Chem. (2004) 47:4559-4569.

Pellicciari et al., "Nongenomic Actions of Bile Acids. Synthesis and Preliminary Characterization of 23- and 6,23-Alkyl-Substituted Bile Acid Derivatives as Selective Modulators for the G-Protein Coupled Receptor TGR5," J. Med. Chem. (2007) 50:4265-4268.

Pellicciari et al., "6 alpha-ethyl-chenodeoxycholic Acid (6-EDCA), a Potent and Selective FXR Agonist Endowed with Anticholestatic Activity," J. Med. Chem. (2002) 45(17):3569-3572.

Pellicciari et al. "Farnesoid X Receptor: From Structure to Potential Clinical Applications", Journal of Medicinal Chemistry (2005), 48 (17), p. 1-21.

(56) References Cited

OTHER PUBLICATIONS

Raskin et al., "A Randomized Trial of Rosiglitazone Therapy in Patients With Inadequately Controlled Insulin-Treated Type 2 Diabetes," Diabetes Care (2001) 24(7):1226-1232.
Roda et al., "23-Methyl-3α,7β-Dihydroxy-5β-cholan-24-oic Acid: Dose-Response Study of Biliary Secretion in Rat," Hepatol. (1988) 8(6):1571-1576.
Roda et al., "Bile Acids with a Cyclopropyl-Containing Side Chain. IV. Physicochemical and Biological Properties of the Four Diastereoisomers of 3α,7β-Dihydroxy-22,23-methylene-5β-cholan-24-oic Acid," J. Lipid Res. (1987) 28(12):1384-1397.
Roda et al. "New 6-substituted bile acids: physico-chemical and biological properties of 6α-methyl ursodeoxycholic acid and 6α-methyl-7-epicholic acid" Journal of Lipid Research (1994), 35(12), 2268-79.
Rubin et al., "Combination Therapy With Pioglitazone and Insulin in Patients with Type 2 Diabetes," Diabetes (1999) 48 (Suppl. 1):A 110 (Abstract Only).
Russell, DW. "Nuclear Orphan Receptors Minireview Control Cholesterol Catabolism", Cell 97:539-542 (1999).
Sato et al., "Novel Potent and Selective Bile Acid Derivatives as TGR5 Agonists: Biological Screening, Structure-Activity Relationships, and Molecular Modeling Studies," J. Med. Chem. (2008) 51(6):1831-1841.
Schmider et al., "Evidence for an additional sinusoidal bile salt transport system," Database Accession No. 2000:260886 (2009).
Seol, W. et al., "Isolation of Proteins That Interact Specifically with the Retinoid X Receptor: Two Novel Orphan Receptors", Molecular Endocrinology, 9:72-85 (1995).
Sinal, C. "Targeted Disruption of the Nuclear Receptor FXR/BAR Impairs Bile Acid and Lipid Homeostasis", Cell 102: 731-744 (2000).
Souillac et al., "Characterization of Delivery Systems, Differential Scanning Calorimetry," Encyclopedia of Controlled Drug Delivery, John Wiley & Sons (1999), pp. 212-227.
Stenner et al., "The Effect of ursodeoxycholic acid on fibrosis markers in alcoholic liver disease," Flak Symposium (2002), pp. 229-235.
Urizar et al., "A Natural Product that Lowers Cholesterol as an Antagonist Ligand for FXR," Science (2002) 296(5573): 1703-1706.
Vippagunta et al., "Crystalline Solids," Advanced Drug Delivery Reviews (2001) 48:3-26.
Willson et al., "The PPARs: From Orphan Receptors to Drug Discovery," J. Med. Chem. (2000) 43(4):527-550.
International Search Report issued for PCT/EP02/01832 dated Jun. 18, 2002.
Aulton, ed. "The Design of Dosage Forms", Pharmaceutics—The Science of Dosage Form Design, 1988, Chapter 1, p. 1-13.
Badger, "Biological Activity of Compounds in Homologous Series", 1946, Nature, No. 4017, p. 585.
Bousquet et al. "Determination of chenodeoxycholic acid in pharmaceutical preparations of ursodeoxycholic acid by high performance liquid chromatography with coulometric electrochemical detection", Journal of Liquid Chromatography & Related Technologies, 1997, vol. 20, No. 5, p. 757-770.
Byrn et al. "Pharmaceutical Solids: A Strategic Approach to Regulatory Considerations", Pharmaceutical Research, 1995, vol. 12, No. 7, p. 945-954.
Chaumeil, "Micronization: A Method of Improving the Bioavailability of Poorly Soluble Drugs," Methods and Findings in Experimental and Clinical Pharmacology, 1998, vol. 20, No. 3, p. 211-215.
Chenodiol Label, Nexgen Pharma, Inc., Rev. Sep. 2019, 9 pages.
Choi et al. "Amorphous Ultrafine Particle Preparation For Improvement of Bioavailability of Insoluble Drugs: Grinding Characteristics of Fine Grinding Mills", International Journal of Mineral Processing, 2004, 74S, p. S165-S172.
Chu et al. "Effect of Particle Size on the Dissolution Behaviors of Poorly Water-soluble Drugs", Archives of Pharmacal Research, 2012, vol. 35, No. 7, p. 1187-1195.
Costantino et al., "Evaluation of Hydrophobic/hydrophilic Balance of Bile Acids by Comparative Molecular Field Analysis (CoMFA)," Steroids, 2000, vol. 65, p. 483-489.
Delalonde et al., "Impact of Physicochemical Environment on the Super Disintegrant Functionality of Cross-Linked Carboxymethyl Sodium Starch: Insight on Formulation Precautions", AAPS PharmSciTech, 2015, vol. 16, No. 2, p. 407-412.
FDA Guidance for Industry Q3A Impurities in New Drug Substances (Jun. 2008), 17 pages.
FDA Guidance, Q6A Specifications: Test Procedures and Acceptance Criteria for New Drug Substances and New Drug Products: Chemical Substances, Federal Register, Dec. 29, 2000, vol. 65, No. 251, p. 83041-83063.
FDA Guidance for Industry, "Manufacturing, Processing, or Holding Active Pharmaceutical Ingredients" Mar. 1998, p. 1-53.
Fujiwara et al. "First-principles and Direct Design Approaches for the Control of Pharmaceutical Crystallization", Journal of Process Control, 2005, vol. 15, p. 493-504.
Harwood L. & Moody C. "Organic Reactions: from Starting Materials to Pure Organic Product", Experimental Organic Chemistry, Principles and Practice, 1989, Chapter 3, p. 67-205.
Hofmann "The Continuing Importance of Bile Acids in Liver and Intestinal Disease" 159 Arch. Intern. Med., 1999, p. 2647-2658.
Hu & Liu, "Quality Control in Pharmaceuticals: Residual Solvents Testing and Analysis", Wide Spectra of Quality Control, 2011, Ch. 11, p. 183-210.
ICH Harmonised Tripartite Guideline—Impurities in New Drug Substances Q3A(R2); Oct. 2006, 15 pages.
Intercept Pharmaceuticals, Inc., Press Release, Intercept Pharmaceuticals' FXR Agonist INT-747 Meets Primary Endpoint in a Phase II Clinical Trial in Type 2 Diabetic Patients with Nonalcoholic Fatty Liver Disease (Oct. 1, 2009), 1 page.
Intercept Pharmaceuticals to Collaborate With NIDDK on Study of Obeticholic Acid (INT-747) in Nonalcoholic Steatohepatitis (NASH), BioSpace (Jul. 28, 2010), 4 pages.
Iverlund et al. "Carbon Cartridges and Their Use as a Purification Step in Pharmaceutical API Processes", Proceedings of European Congress of Chemical Engineering (ECCE-6) Copenhagen Sep. 16-20, 2007, 13 pages.
Kawabata et al. "Formulation design for poorly water-soluble drugs based on biopharmaceutics classification system: Basic approaches and practical applications", International Journal of Pharmaceutics, 2011, vol. 420, p. 1-10.
Kim et al. "Bile acid sulfonate and 7-alkylated bile acid analogs: Effect on intestinal absorption of taurocholate and cholesterol 7α-hydroxylase activity in cultured rat hepatocytes", Steroids, 2000, vol. 65, Issue 1, p. 24-28.
Kottke & Rudnic "Tablet dosage forms", Modern Pharmaceutics, Revised & Expanded 4th Edition, 2002, Chapter 10, p. 287-333.
Krishnaiah "Pharmaceutical Technologies for Enhancing Oral Bioavailability of Poorly Soluble Drugs", Journal of Bioequivalence & Bioavailability, 2010, vol. 2, Issue 2, p. 28-36.
Kuroki et al. "7-Methyl bile acids: 7β-methyl-cholic acid inhibits bacterial 7-dehydroxylation of cholic acid and chenodeoxycholic acid in the hamster", Journal of Lipid Research, 1987, vol. 28, p. 856-863.
Lieberman et al. "Preformulation Testing", Pharmaceutical Dosage Forms: Tablets, 1989, vol. 1, Ch. 1, 2d ed., p. 1-73.
Li et al. "The Role of Intra- and Extragranular Microcrystalline Cellulose in Tablet Dissolution", Pharmaceutical Development and Technology, 1996, vol. 1, No. 4. p. 343-355.
Makishima et al. "Identification of a Nuclear Receptor for Bile Acids", Science, 1999, vol. 284, p. 1362-1365.
Markarian "Using Micronization to Reduce API Particle Size", PharmaTech.com, Jan. 16, 2013, 3 pages.
Mason et al. "Farnesoid-X Receptor Agonists: A New Class of Drugs For the Treatment of PBC? An International Study Evaluating the Addition of INT-747 to Ursodeoxycholic Acid", Journal of Hepatology, 2010, vol. 52, p. S1-S2.
Natalini et al. "Correlation between CMC and chromatographic index: simple and effective evaluation of the hydrophobic/hydrophilic balance of bile acids", Anal. Bioanal. Chem., 2007, vol. 388, p. 1681-1688.

(56) References Cited

OTHER PUBLICATIONS

Ng et al. "Suitability of [11,12-$^3H_2$]chenodeoxycholic Acid and [11,12-$^3H_2$]lithocholic Acid For Isotope Dilution Studies of Bile Acid Metabolism In Man", 1977, Journal of Lipid Research, vol. 18, p. 753-758.
Pavia et al., "Technique 5—Crystallization: Purification of Solids", Organic Laboratory Techniques, 1st Ed., 1998, p. 648-665.
Porez et al., "Bile acid receptors as targets for the treatment of dyslipidemia and cardiovascular disease", Journal of Lipid Research, 2012, vol. 53, p. 1723-1737.
Rajevic et al. "Assay of Ursodeoxycholic Acid and Related Impurities in Pharmaceutical Preparations by HPLC With Evaporative Light Scattering Detector", J. Liq. Chrom. & Rel. Technol., 1998, vol. 21, No. 18, p. 2821-2830.
Roda et al. " Structure-activity relationship studies of new 6α-methyl and 6α-fluoro-ursodeoxycholic acid derivatives", Falk Symposium, Bile Acids in Gastroenterology, Basic and Clinical Advances, 1995, vol. 80, p. 27-37.
Roda et al. "HPLC study of the impurities present in different ursodeoxycholic acid preparations: comparative evaluation of four detectors", Journal of Pharmaceutical & Biomedical Analysis, 1993, vol. 11, No. 8, p. 751-760.
Rohani "Applications of the Crystallization Process in the Pharmaceutical Industry", Front. Chem. Eng. China, 2010, vol. 4, No. 1, p. 2-9.
Savjani et al., "Drug Solubility: Importance and Enhancement Techniques," Internaional Scholarly Research Network, ISRN Pharmaceutics, 2012, vol. 2012, Article ID 195727, 10 pages.
Scalia et al. "Assay of free bile acids in pharmaceutical preparations by HPLC with electrochemical detection", International Journal of Pharmaceutics, 1995, vol. 115, p. 249-253.
Shotton et al. "Effect of Intragranular and Extragranular Disintegrating Agents on Particle Size of Disintegrated Tablets", 1976, Journal of Pharmaceutical Sciences, p. 1170-1174.
Silverman et al. "Drug Discovery, Design, and Development", The Organic Chemistry of Drug Design and Drug Action, First Edition, 1992, Chapter 2, p. 4-51.
Snyder et al. "Preparative HPLC Separation", Practical HPLC Method Development, Second Edition, 1997, Chapter 13, p. 616-642.
Study NCT00550862, A Study of INT 747 (6-ECDCA) in Combination With Ursodeoxycholic Acid (URSO®, UDCA) in Patients With Primary Biliary Cirrhosis, Oct. 27, 2007, 7 pages.
Study NCT01265498, The Farnesoid X Receptor (FXR) Ligand Obeticholic Acid in NASH Treatment (FLINT) Trial, Dec. 21, 2010, 11 pages.
Takahashi et al. "Using Fluid Bed Granulation to Improve the Dissolution of Poorly Water-Soluble Drugs", Brazilian Archives of Biology and Technology, 2012, vol. 55, No. 3, p. 477-484.
Takata et al. "Cocrystal Screening of Stanolone and Mestanolone Using Slurry Crystallization", Crystal Growth & Design, 2008, vol. 8, No. 8, p. 3032-3037.
Une et al. "Synthesis of bile acid analogs: 7-alkylated chenodeoxycholic acids", Steroids, 1989, vol. 53/1-2, p. 97-105.
Vranic "Amorphous Pharmaceutical Solids", Bosnian Journal of Basic Medical Sciences, 2004, vol. 4, No. 3, p. 35-39.
Wang et al. "Endogenous Bile Acids Are Ligands for the Nuclear Receptor FXR/BAR", Molecular Cell, 1999, vol. 3, p. 543-553.
Yang et al. "Physical Factors Contributing to Hydrophobic Constant π", Quant. Struct. Act. Relat., 1986, vol. 5, p. 12-18.
Yu "Amorphous pharmaceutical solids: preparation, characterization and stabilization," Advanced Drug Delivery Reviews, 2001, vol. 48, p. 27-42.
Yu et al., "An improved synthesis of 6α-ethylchenodeoxycholic acid (6ECDCA), a potent and selective agonist for the Farnesoid X Receptor (FXR)," Steroids, 2012, vol. 77, p. 1335-1338.

* cited by examiner

STEROIDS AS AGONISTS FOR FXR

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

The present invention relates to Farnesoid X receptors (FXR). More particularly, the present invention relates to compounds useful as agonists for FXR, pharmaceutical formulations comprising such compounds, and therapeutic use of the same.

Farnesoid X Receptor (FXR) is an orphan nuclear receptor initially identified from a rat liver cDNA library (BM. Forman, et al., Cell 81:687-693 (1995)) that is most closely related to the insect ecdysone receptor. FXR is a member of the nuclear receptor family of ligand-activated transcription factors that includes receptors for the steroid, retinoid, and thyroid hormones (DJ. Mangelsdorf, et al., Cell 83:841-850 (1995)). Northern and in situ analysis show that FXR is most abundantly expressed in the liver, intestine, kidney, and adrenal (BM. Forman, et al., Cell 81:687-693 (1995) and W. Seol, et al., Mol. Endocrinnol. 9:72-85 (1995)). FXR binds to DNA as a heterodimer with the 9-cis retinoic acid receptor (RXR). The FXR/RXR heterodimer preferentially binds to response elements composed of two nuclear receptor half sites of the consensus AG(G/T)TCA organized as an inverted repeat and separated by a single nucleotide (IR-1 motif) (BM. Forman, et al., Cell 81:687-693 (1995)). An early report showed that rat FXR is activated by micromolar concentrations of farnesoids such as farnesol and juvenile hormone (BM. Forman, et al., Cell 81:687-693 (1995)). However, these compounds failed to activate the mouse and human FXR, leaving the nature of the endogenous FXR ligand in doubt. Several naturally-occurring bile acids bind to and activate FXR at physiological concentrations (PCT WO 00/37077, published 29 Jun. 2000)). As discussed therein, the bile acids that serve as FXR ligands include chenodeoxycholic acid (CDCA), deoxycholic acid (DCA), lithocholic acid (LCA), and the taurine and glycine conjugates of these bile acids.

Bile acids are cholesterol metabolites that are formed in the liver and secreted into the duodenum of the intestine, where they have important roles in the solubilization and absorption of dietary lipids and vitamins. Most bile acids (~95%) are subsequently reabsorbed in the ileum and returned to the liver via the enterohepatic circulatory system. The conversion of cholesterol to bile acids in the liver is under feedback regulation: Bile acids down-regulate the transcription of cytochrome P450 7a (CYP7a), which encodes the enzyme that catalyzes the rate limiting step in bile acid biosynthesis. There are data to suggest that FXR is involved in the repression of CYP7a expression by bile acids, although the precise mechanism remains unclear (DW. Russell, Cell 97:539-542 (1999)). In the ileum, bile acids induce the expression of the intestinal bile acid binding protein (IBABP), a cytoplasmic protein which binds bile acids with high affinity and may be involved in their cellular uptake and trafficking. Two groups have now demonstrated that bile acids mediate their effects on IBABP expression through activation of FXR, which binds to an IR-1 type response element that is conserved in the human, rat, and mouse IBABP gene promoters (14; 17). Thus FXR is involved in both the stimulation (IBABP) and the repression (CYP7a) of target genes involved in bile acid and cholesterol homeostasis.

European Patent No. 0 312 867, published 05 May 1992 to Giuliana S.p.A. describes 6-methyl derivatives of natural biliary acids such as ursodeoxycholic acid, ursocholic acid, chenodeoxycholic acid and cholic acid.

BRIEF SUMMARY OF THE INVENTION

According to a first aspect, the present invention provides compounds of formula I:

(I)

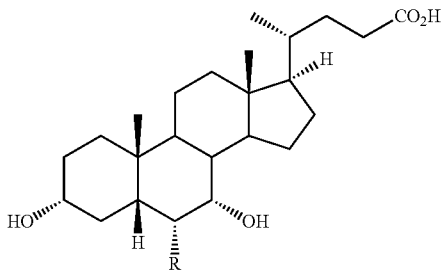

wherein R is ethyl, and pharmaceutically acceptable salts, solvates or amino acid conjugates thereof. In one preferred embodiment, the compound of formula (I) is in the form of the glycine or taurine conjugate.

In another aspect, the present invention provides 3α,7α-dihydroxy-6α-ethyl-5β-cholan-24-oic acid and pharmaceutically acceptable salts, solvates or amino acid conjugates thereof.

In another aspect, the present invention provides 3α,7α-dihydroxy-6α-allyl-5β-cholan-24-oic acid and pharmaceutically acceptable salts, solvates or amino acid conjugates thereof.

In another aspect, the present invention provides compounds which are FXR agonists.

In another aspect, the present invention provides a pharmaceutical formulation comprising a compound of formula (I) and a pharmaceutically acceptable carrier or diluent.

In another aspect, the present invention provides a method for the prevention or treatment of an FXR mediated disease or condition. The method comprises administering a therapeutically effective amount of a compound of formula (I). The present invention also provides the use of a compound of formula (I) for the preparation of a medicament for the prevention or treatment of an FXR mediated disease or condition.

In another aspect, the present invention provides a method for the prevention or treatment of cardiovascular disease. The method comprises administering a therapeutically effective amount of a compound of formula (I). The present invention also provides the use of a compound according to claim 1 for the preparation of a medicament for the prevention or treatment of cardiovascular disease. In one embodiment, the cardiovascular disease is atherosclerosis.

In another aspect, the present invention provides a method for increasing HDL cholesterol. The method comprises administering a therapeutically effective amount of a compound of formula (I). The present invention also provides the use of a compound according to claim 1 for the preparation of a medicament for increasing HDL-cholesterol.

In another aspect, the present invention provides a method for lowering triglycerides. The method comprises administering a therapeutically, effective amount of a compound of formula (I). The-present invention also provides the use of a compound according to claim 1 for the preparation of a medicament for lowering triglycerides.

In another aspect, the present invention provides a method for the prevention or treatment of cholestatic liver disease. The method comprises administering a therapeutically effective amount of a compound of formula (I). The present invention also provides the use of a compound according to claim 1 for the preparation of a medicament for the prevention or treatment of cholestatic liver diseases.

In another aspect, the present invention provides a radiolabeled compound of formula (I). In one embodiment, the compound of formula (I) is tritiated.

In another aspect, the present invention provides a process for preparing a compound of formula (I) and pharmaceutically acceptable salts, solvates or amino acid conjugates thereof. The process comprises the steps of:

a) reacting 3α-hydroxy-7-keto-5β-cholan-24-oic acid with 3,4-dihydropyrane to prepare 3α-tetrahydropyranyloxy-7-keto-5β-cholan-24-oic acid;

b) reacting 3α-tetrahydropyranyloxy-7-keto-5β-cholan-24-oic acid with an alkyl bromide of the formula R—Br where R is ethyl to prepare a compound of formula (II)

II

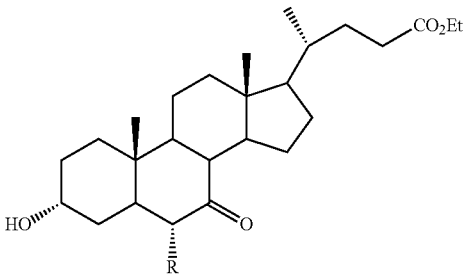

wherein R is ethyl;

c) reacting the compound of formula (II) with sodium borohydride to prepare a compound of formula (III)

III

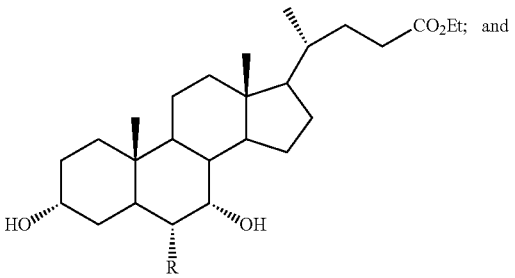

d) reacting the compound of formula (III) with sodium hydroxide to prepare the compound of formula (I).

Further aspects of the present invention are described in the detailed description of the invention, examples, and claims which follow.

DETAILED DESCRIPTION OF THE INVENTION

The present invention provides compounds of formula I:

(I)

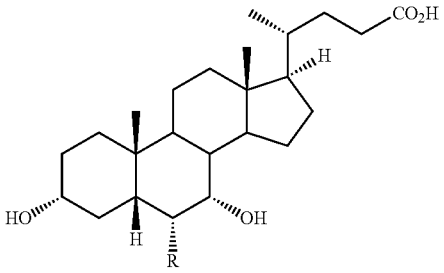

wherein R is ethyl and pharmaceutically acceptable salts, solvates or amino acid conjugates thereof.

Suitable pharmaceutically acceptable salts according to the present invention will be readily determined by one skilled in the art and will include, for example, basic salts such as metallic salts made from aluminium, calcium, lithium, magnesium, potassium, sodium, and zinc or organic salts made from N,N'-dibenzylethylenediamine, chlorprocaine, choline, diethanolamine, ethylendiamine, meglumine (N-methylglucamine), and procaine. Such salts of the compounds of formula (I) may be prepared using conventional techniques, from the compound of Formula (I) by reacting, for example, the appropriate base with the compound of Formula (I).

When used in medicine, the salts of a compound of formula (I) should be pharmaceutically acceptable, but pharmaceutically unacceptable salts may conveniently be used to prepare the corresponding free base or pharmaceutically acceptable salts thereof.

As used herein, the term "solvate" is a crystal form containing the compound of formula (I) or a pharmaceutically acceptable salt thereof and either a stoichiometric or a non-stoichiometric amount of a solvent. Solvents, by way of example, include water, methanol, ethanol, or acetic acid. Hereinafter, reference to a compound of formula (I) is to any physical form of that compound, unless a particular form, salt or solvate thereof is specified.

As used herein, the term "amino acid conjugates" refers to conjugates of the compounds of formula (I) with any suitable amino acid. Preferably, such suitable amino acid conjugates of the compounds of formula (I) will have the added advantage of enhanced integrity in bile or intestinal fluids. Suitable amino acids include but are not limited to glycine and taurine. Thus, the present invention encompasses the glycine and taurine conjugates of any of the compounds of formula (I).

Preferred compounds of formula (I) include compounds selected from the group consisting of 3α,7α-dihydroxy-6α-ethyl-5β-cholan-24-oic acid and their pharmaceutically acceptable salts, solvates or amino acid conjugates thereof.

Hereinafter all references to "compounds of formula (I)" refer to compounds of formula (I) as described above together with their and pharmaceutically acceptable salts, solvates or amino acid conjugates thereof.

Preferably, the compounds of formula (I) are FXR agonists. As used herein, the term "agonist" refers to compounds which achieve at least 50% activation of FXR relative to CDCA, the appropriate positive control in the assay methods described in PCT Publication No. WO 00/37077 published 29 Jun. 2000 to Glaxo Group Limited, the subject matter of which is incorporated herein by reference in its entirety. More preferably, the compounds of this invention achieve 100% activation of FXR in the scintillation proximity assay or the HTRF assay as described in PCT Publication No. WO 00/37077.

The compounds of the formula (I) are useful for a variety of medicinal purposes. The compounds of formula (I) may be used in methods for the prevention or treatment of FXR mediated diseases and conditions. FXR mediated diseases or conditions include cardiovascular diseases including atherosclerosis, arteriosclerosis, hypercholesteremia, and hyperlipidemia. In particular, the compounds of formula (I) are useful in the treatment and prevention of cardiovascular disease including atherosclerosis and hypercholesteremia. The compounds of formula (I) are also useful for increasing HDL-cholesterol, and lowering triglycerides.

In addition, the compounds of the present invention are useful for the prevention and treatment of cholestatic liver diseases. The compounds of the present invention increase the flow of bile acid. Increased flow of bile acids improves the flux of bile acids from the liver to the intestine. See, C. Sinal, Cell 102: 731-744 (9000). Essentially, FXR null mice demonstrate that FXR plays a central role in bile acid homeostasis, and is therefore critical to lipid homeostasis by virtue of the regulation of enzymes and transporters that are critical to lipid catabolism and excretion. FXR therefore is an important target for the treatment of a number of cholestatic liver disease and other lipid related diseases and conditions.

The methods of the present invention are useful for the treatment of mammals generally and particularly humans.

The methods of the present invention comprise the step of administering a therapeutically effective amount of the compound of formula (I). As used herein, the term "therapeutically effective amount" refers to an amount of the compound of formula (I) which is sufficient to achieve the stated effect. Accordingly, a therapeutically effective amount of a compound of formula (I) used in the method for the prevention or treatment of FXR mediated diseases or conditions will be an amount sufficient to prevent or treat the FXR mediated disease or condition. Similarly, a therapeutically effective amount of a compound of formula (I) for use in the method for the prophylaxis or treatment of cholestatic liver diseases or increasing bile flow will be an amount sufficient to increase bile flow to the intestine.

The amount of a compound of formula (I) or pharmaceutically acceptable salt or solvate thereof, which is required to achieve the desired biological effect will depend on a number of factors such as the use for which it is intended, the means of administration, and the recipient, and will be ultimately at the discretion of the attendant physician or veterinarian. In general, a typical daily dose for the treatment of FXR mediated diseases and conditions, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including the prophylaxis and treatment of cholestatic liver diseases.

Thus in a further aspect the present invention provides pharmaceutical compositions comprising, as active ingredient, a compound of formula (I) or a pharmaceutically acceptable salt or solvate thereof, together with at least one pharmaceutical carrier or diluent. These pharmaceutical compositions may be used in the prophylaxis and treatment of the foregoing diseases or conditions and in cardiovascular therapies as mentioned above.

The carrier must be pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient. If desired other physiologically active ingredients may also be incorporated in the pharmaceutical compositions of the invention.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound, but where possible, oral administration is preferred for the prevention and treatment of FXR mediated diseases and conditions.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavoured base, such as sugar and acacia or tragacanth and pastilles comprising the active compound in an inert base, such as gelatine and glycerine or sucrose acacia.

Formulations suitable for parenteral administration typically comprise sterile aqueous solutions containing a predetermined concentration of the active compound; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Suitable formulations for administration by inhalation include fine particle dusts or mists which may be generated by means of various types of metered dose pressurised aerosols, nebulisers, or insufflators.

For pulmonary administration via the mouth, the particle size of the powder or droplets is typically in the range 0.5-10 μm, preferably 1-5 μm, to ensure delivery into the bronchial tree. For nasal administration, a particle size in the range 10-500 μm is preferred to ensure retention in the nasal cavity.

Metered dose inhalers are pressurised aerosol dispensers, typically containing a suspension or solution formulation of the active ingredient in a liquefied propellant. During use, these devices discharge the formulation through a valve adapted to deliver a metered volume, typically from 10 to 150 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavouring agents.

Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavouring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art of pharmacy, having regard for the type of formulation in issue. For example, formulations suitable for oral administration may include flavouring agents and formulations suitable for intranasal administration may include perfumes.

Therefore, according to a further aspect of the present invention, there is provided the use of a compound of formula (I) in the preparation of a medicament for the prevention or treatment of FXR mediated diseases or conditions.

Compounds of the invention can be made according to any suitable method of organic chemistry. According to one method, compounds of formula (I) are prepared using the synthesis process as depicted in Scheme 1:

Scheme 1

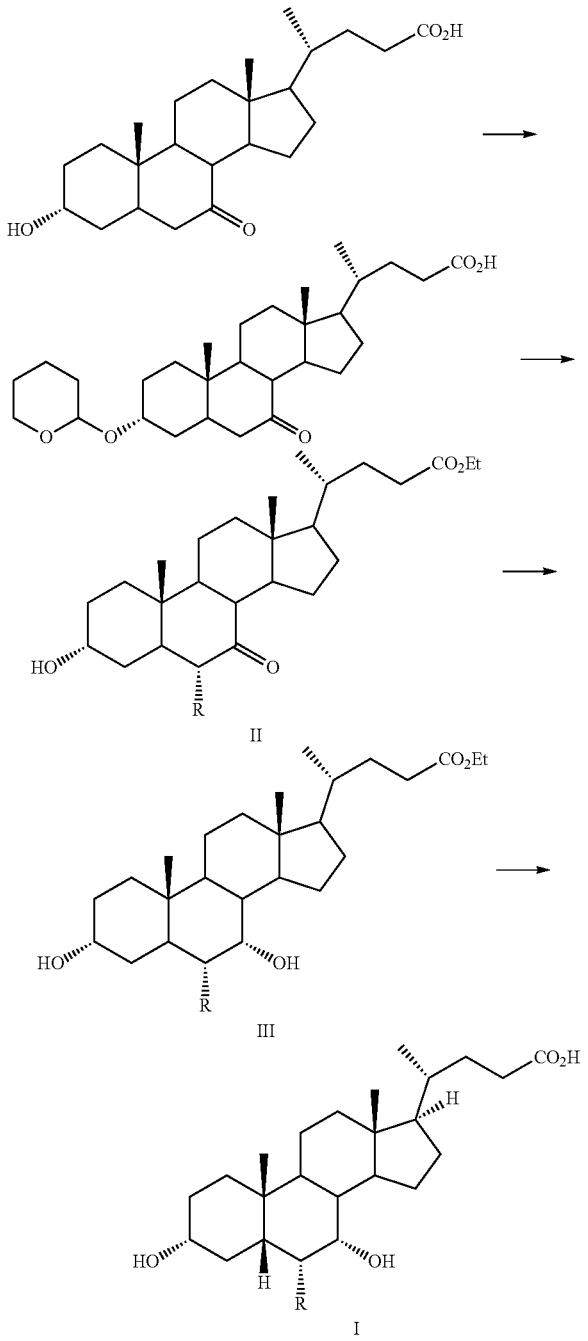

wherein R is ethyl.

Generally, the compounds of the present invention can be prepared by the process comprising a) reacting 3α-hydroxy-7-keto-5β-cholan-24-oic acid with 3,4-dihydropyrane to prepare 3α-tetrahydropyranyloxy-7-keto-5β-cholan-24-oic acid; b) reacting 3α-tetrahydropyranyloxy-7-keto-5β-cholan-24-oic acid with an alkyl bromide of the formula R—Br where R is ethyl to prepare a compound of formula (II); c) reacting the compound of formula (II) with sodium borohydride to prepare a compound of formula (III); d) reacting the compound of formula (III) with sodium hydroxide to prepare the compound of formula (I).

More particularly, the compounds of formula (I) are conveniently prepared by reacting the compounds of formula (III) with sodium hydroxide in a suitable solvent at ambient temperature. Suitable solvents include lower alcohols, such as ethanol. The reaction mixture may optionally be acidified with an appropriate acid such as hydrochloric acid.

The compounds of formula (III) are conveniently prepared by reacting compounds of formula (II) with sodium borohydride in a suitable solvent at ambient temperature. Suitable solvents include lower alcohols such as ethanol.

The compounds of formula (II) are conveniently prepared by reacting 3α-tetrahydropyranyloxy-7-keto-5β-cholan-24-oic acid with an alkyl bromide of the formula R—Br where R is ethyl in a suitable solvent and in the presence of n-Butyl lithium and HMPA in diisopropylamine. Polar solvents such as tetrahydrofuran are useful for conducting the reaction. Preferably, the reaction is carried out at cold temperatures such as about −70 to −80° C.

3α-Tetrahydropyranyloxy-7-keto-5β-cholan-24-oic acid can conveniently be prepared from 3α-hydroxy-7-keto-5β-cholan-24-oic acid by reacting with 3,4-dihydropyrane in p-toluenesulfonic acid.

Pharmaceutically acceptable salts, solvates and amino acid conjugates of the compounds of formula (I) can be prepared from the free base using methods known to those skilled in the art.

The present invention also provides radiolabeled compounds of formula (I). Radiolabeled compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I). In one preferred embodiment, the compounds of formula (I) are tritiated.

The radiolabeled compounds of formula (I) are useful in assays for the lo identification of compounds which interact with FXR such as those described in PCT Publication No. WO 00/37077 already incorporated herein.

The following examples are intended for illustration only and are not intended to limit the scope of the invention in any way, the present invention being defined by the claims.

EXAMPLE

Synthesis of 3α7α-Dihydroxy-6α-ethyl-5β-cholan-24-oic Acid (6αEt-CDCA)

3α-Tetrahydropyranyloxy-7-keto-5β-cholan-24-oic acid p-Toluensulfonic acid (6.0 g, 3.2 mmol) and 3,4-dihydro-2H-pyrane (4.6 g, 54 mmol) were added to a solution of 3α-hydroxy-7-keto-5β-cholan-24-oic acid (1) (6.0 g, 14.4 mmol) in 120 ml of dioxane. The reaction mixture was stirred at room temperature for 15 min and then was treated with methanol saturated with ammonia until it reached pH of about 8-9. The solvents were removed under vacuum and the residue was extracted with chloroform (200 ml) and washed with a saturated $NaHCO_3$ solution (2×50 ml). After drying over anhydrous $Na_2SO_4$ and evaporation under vacuum, the residue was purified by silica gel chromatography. Elution by $CHCl_3$:MeOH (90:10) yielded 5.4 g (10.4 mmol, 74% yield) of compound 2 as a white solid (mp: 157-159° C.).

$^1$H-NMR ($CDCl_3$) δ: 0.58 (s, 3H, $CH_3$-18); 0.88 (d, J=6.1 Hz, 3H, $CH_3$-21); 1.14 (s, 3H, $CH_3$-19); 3.3-3.7 (m, 3H, pyr); 3.75-3.95 (m, 1H, pyr); 4.64-4.71 (m, 1H, CH-3).

Ethyl 3α-hydroxy-6α-ethyl-7-keto-5β-cholan-24-oate.

n-Butyl lithium (21.1 ml, 1.6M solution in hexane) and HMPA (4.3 ml) were added dropwise at −78° C. to a solution of diisopropylamine (4.1 ml, 33.7 mmol) in 250 ml of dry THF. The system was held at −78° C. for an additional 30 min and then, 3α-tetrahydropyranyloxy-7-keto-5β-cholan-24-oic acid (2) (5 g, 10.5 mmol) dissolved in 50 ml of dry THF was cooled to −78° C. and added dropwise to the mixture. After 20 minutes ethyl bromide (7.8 ml, 105 mmol) dissolved in THF (20 ml) was slowly added and the mixture was allowed to come to room temperature overnight. The solvents were removed under vacuum, acidified by 10% HCl and extracted with ethyl acetate (5×200 ml), and washed with a saturated NaCl solution (1×200 ml). After drying over anhydrous $Na_2SO_4$ and evaporation under vacuum, the crude residue was refluxed with a solution of 2N HCl in EtOH (50 ml) for 12 hours. The residue was evaporated under vacuum and extracted with ethyl acetate (300 ml), washed with a saturated $NaHCO_3$ solution (2×100 ml), dried with $Na_2SO_4$ and evaporated under vacuum. The residue was purified by silica gel chromatography; elution by light petroleum:ethyl acetate (70:30) yielded 0.57 g (1.27 mmol, 12% yield) of ethyl 3α-hydroxy-6α-ethyl-7-keto-5β-cholan-24-oate (3) as an amorphous solid.

$^1$H-NMR ($CDCl_3$) δ: 0.50 (s, 3H, $CH_3$-18); 0.69 (t, J=7.3 Hz, 3H, $CH_2$—$\underline{CH_3}$); 0.82 (d, J=6.2 Hz, 3H, $CH_3$-21); 1.06-1.18 (m, 8H, $CO_2$ $CH_2\underline{CH_3}$+$\underline{CH_2}$—$CH_3$+$CH_3$-19); 3.36-3.42 (m, 1H, CH—OH), 4.01 (q, J=7.2, Hz 2H, $CO_2$ $\underline{CH_2}CH_3$).

Ethyl 3α,7α-dihydroxy-6α-ethyl-5β-cholan-24-oate.

Ethyl 3α-hydroxy-6α-ethyl-7-keto-5β-cholan-24-oate (3) (0.185 g, 0.4 mmol) was dissolved in 30 ml of 96% EtOH and treated with $NaBH_4$ (30 mg, 0.8 mmol). The mixture was stirred at room temperature for 2 hours. Water (10 ml) was then added and the mixture was partially concentrated under vacuum and extracted with ethyl acetate (3×20 ml). The combined organic fractions were washed with a saturated NaCl solution (1×50 ml), dried with $Na_2SO_4$ and evaporated under vacuum. To give ethyl 3 α,7α-dihiydroxy-6α-ethyl-5β-cholan-24-oate (4) (0.15 g, 0.33 mmol, 81% yield) as white solid (mp: 55-57° C.).

$^1$H-NMR ($CDCl_3$) δ: 0.62 (s, 3H, $CH_3$-18); 0.84-0.92 (m, 9H, $CH_2$—$\underline{CH_3}$+$CH_3$-19+$CH_3$-21); 1.22 (t, J=7.2 Hz, 3H, $CO_2$ $CH_2\underline{CH_3}$); 3.30-3.47 (m, 1H, CH-3), 3.66 (brs, 1H, CH-7); 4.08 (q, J=7.2, Hz 2H, $CO_2$ $\underline{CH_2}CH_3$).

3α,7α-Dihydroxy-6α-ethyl-5β-cholan-24-oic acid.

Ethyl 3α,7α-dihydroxy-6α-ethyl-5β-cholan-24-oate (4) (0.10 g, 0.22 mmol) was dissolved in 15 ml of 96% EtOH and added to 10% NaOH in 96% EtOH (2 ml, 5 mmol). The mixture was refluxed for 4 hours. The mixture was acidified with 3N HCl and extracted with ethyl acetate (3×20 ml). The combined organic fractions were washed with a saturated NaCl solution (1'50 ml), dried with $Na_2SO_4$ and evaporated under vacuum. The residue was chromatographed on silica gel column; elution by $CHCl_3$:MeOH (95:5) yielded 3α,7α-dihydroxy-6α-methyl-5β-cholan-24-oic acid (6) (0.04 g, 0.095 mmol, 43% yield).

$^1$H-NMR ($CDCl_3$) δ: 0.67 (s, 3H, $CH_3$-18); 0.90-0.96 (m, 9H, $CH_2$—$\underline{CH_3}$+$CH_3$-19+$CH_3$-21); 2.22-2.46 (2m, 2H, $CH_2$-23); 3.39-3.47 (m, 1H, CH-3), 3.72 (brs, 1H, CH-7).

$^{13}$C-NMR ($CDCl_3$) δ: 11.65, $CH_2\underline{CH_3}$-6; 11.80, C-18; 18.25, C-21, 20.76, C-11; 22.23, $\underline{CH_2}CH_3$-6; 23.14, C-19; 23.69, C-15; 28.17, C-16; 30.53, C-2; 30.81, C-22; 30.95, C-23; 33.23, C-9; 33.90, C-10; 35.38, C-20; 35.52, C-1; 35.70, C-4; 39.60, C-12; 40.03, C-5; 41.19, C-6; 42.77, C-13; 45.19, C-8; 50.49, C-14; 55.80, C-17; 70.97, C-7; 72.38, C-3; 179.19, C-24.

The invention claimed is:

1. A compound of [formula I] *formula (I)*:

(I)

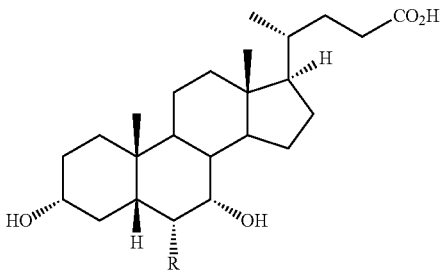

wherein R is ethyl and pharmaceutically acceptable salts, solvates or amino acid conjugates thereof.

2. The glycine conjugate of a compound of formula (I):

(I)

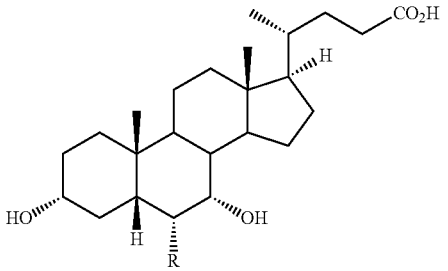

wherein R is ethyl.

3. The taurine conjugate of a compound of formula (I):

(I)

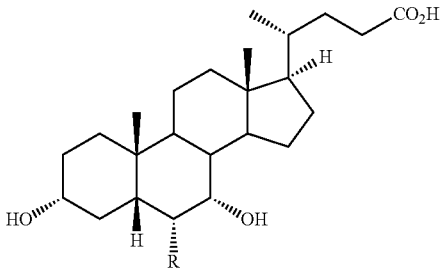

wherein R is ethyl.

4. A pharmaceutical formulation comprising a compound according to claim 1 and a pharmaceutically acceptable carrier or diluent.

5. A method for the treatment of an FXR mediated disease or condition in a mammal comprising administering to a mammal suffering from an FXR mediated disease or condition a therapeutically effective amount of a compound according to claim 1, wherein said FXR mediated disease or condition is selected from the group consisting of hypercholesteremia, hyperlipidemia, low HDL-cholesterol, and high triglycerides.

6. A method for the treatment of cardiovascular disease in a mammal comprising administering to a mammal suffering from a cardiovascular disease a therapeutically effective amount of a compound according to claim 1, wherein said cardiovascular [desease] *disease* is selected from the group consisting of [artherosclerosis] *atherosclerosis* and hypercholesteremia.

7. The method according to claim 6, wherein said cardiovascular disease is atherosclerosis.

8. A method for increasing HDL cholesterol in a mammal, said method comprising administering to a mammal whose HDL cholesterol is to be increased a therapeutically effective amount of a compound according to claim 1.

9. A method for lowering triglycerides in a mammal, said method comprising administering to a mammal whose triglycerides are to be decreased a therapeutically effective amount of a compound according to claim 1.

10. The compound of claim 1, wherein said compound is radiolabeled.

11. The compound of claim 10, wherein said compound is tritiated.

*12. The compound of claim 1, which is the compound of formula (I)*

*(I)*

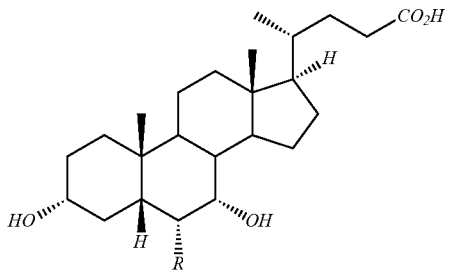

*wherein R is ethyl.*

*13. A pharmaceutically acceptable salt of the compound of claim 1.*

*14. A solvate of the compound of claim 1.*

* * * * *